(12) United States Patent
Nagano

(10) Patent No.: US 10,413,269 B2
(45) Date of Patent: Sep. 17, 2019

(54) RADIOGRAPHIC IMAGE PHOTOGRAPHING SYSTEM

(71) Applicant: KONICA MINOLTA, INC., Chiyoda-ku, Tokyo (JP)

(72) Inventor: Shigeo Nagano, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 156 days.

(21) Appl. No.: 15/354,687

(22) Filed: Nov. 17, 2016

(65) Prior Publication Data
US 2017/0215831 A1   Aug. 3, 2017

(30) Foreign Application Priority Data

Feb. 3, 2016   (JP) ................. 2016-018560

(51) Int. Cl.
*A61B 6/00* (2006.01)
*A61B 6/06* (2006.01)

(52) U.S. Cl.
CPC ............... *A61B 6/542* (2013.01); *A61B 6/06* (2013.01); *A61B 6/405* (2013.01); *A61B 6/4266* (2013.01); *A61B 6/486* (2013.01); *A61B 6/50* (2013.01); *A61B 6/5205* (2013.01); *A61B 6/5258* (2013.01)

(58) Field of Classification Search
CPC .................. A61B 6/405; A61B 6/542
See application file for complete search history.

(56) References Cited

U.S. PATENT DOCUMENTS

2004/0062341 A1*   4/2004   Popescu ................. A61B 6/032
378/4

FOREIGN PATENT DOCUMENTS

| JP | 2001305232 A | 10/2001 |
|---|---|---|
| JP | 2002253541 A | 9/2002 |

* cited by examiner

*Primary Examiner* — Dani Fox
(74) *Attorney, Agent, or Firm* — Holtz, Holtz & Volek PC

(57) ABSTRACT

A radiographic image photographing system includes: a radiation generating device configured to emit radiation; a radiographic image photographing device including a plurality of radiation detecting elements arranged in a two-dimensional pattern and configured to read signal values from the radiation detecting elements; a dose detecting unit arranged between the radiation generating device and the subject and configured to detect a dose of radiation emitted to the subject; and a control unit configured to control the radiation generating device such that the dose of the radiation emitted to the subject becomes a target dose, wherein the control unit sets a tube current or a mAs value of the radiation generating device such that the dose of the radiation becomes the target dose, and corrects and sets the tube current or the mAs value in a case where a difference occurs between the dose of the radiation detected and the target dose.

2 Claims, 7 Drawing Sheets

RADIOGRAPHIC IMAGE PHOTOGRAPHING SYSTEM

The entire disclosure of Japanese Patent Application No. 2016-018560 filed on Feb. 3, 2016 including description, claims, drawings, and abstract are incorporated herein by reference in its entirety.

BACKGROUND OF THE INVENTION

Field of the Invention

The present invention relates to a radiographic image photographing system and particularly, to a radiographic image photographing system photographing a plurality of radiographic images by emitting radiation onto a subject a plurality of number of times.

Description of the Related Art

In place of a conventional film/screen or stimulable phosphor plate, as a device photographing a radiographic image, a radiographic image photographing device (also called a flat panel detector, a semiconductor image sensor, or the like), in which a plurality of radiation detecting elements are arranged in a two-dimensional pattern (matrix pattern), reading electric charge generated inside each radiation detecting element as a signal value through emission of radiation has been developed.

In the conventional film/screen or stimulable phosphor plate, in a case where radiation is emitted thereonto a plurality of number of times, a problem of double exposure or multiple-exposure occurs. However, a radiographic image photographing device can continuously perform photographing, for example, by storing a detected signal value in a memory arranged inside the device or transmitting the signal value to the outside for each photographing process. In this way, by using the radiographic image photographing device, dynamic-state photographing or the like can be performed by emitting radiation to a photographing portion of a subject a plurality of number of times.

In the dynamic-state photographing, for example, in a case where photographing is performed by emitting radiation a plurality of number of times onto the chest of a patient who is a subject as a photographing portion, for example, as illustrated in FIG. 8, radiographic images (in other words, each frame image configuring a dynamic-state image of time phases $T(T=t_0$ to $t_6)$ of a lung field R of the patient can be acquired, and, by analyzing such frame images, a maximal inspiratory level, a maximal expiratory level, an expiratory period, an inspiratory period, and the like of the lung field R can be calculated. Applications to diagnoses have been attempted by further analyzing such a dynamic-state image.

Targets to which the present invention is applied are not only such dynamic-state photographing, but also include, for example, ordinary moving-image photographing, tomosynthesis photographing, photographing using a dual energy subtraction method, and long-object photographing performed by emitting radiation a plurality of number of times while moving a radiographic image photographing device. Thus, any photographing acquiring a plurality of radiographic images by emitting radiation onto a subject a plurality of number of times is a target for the present invention.

In this way, in a case where a plurality of radiographic images are photographed by emitting radiation onto a patient who is a subject a plurality of number of times, when a dose of the emitted radiation varies for each emission, for example, in the case of the moving-image photographing, the brightness levels of frame images configuring a moving image are changed for each frame image, and it is very difficult to view the image.

In addition, for example, in the dynamic-state photographing illustrated in FIG. 8, by analyzing the brightness level of each frame image, the amount of air, the amount of the blood stream, and the like received into a lung field R, can be acquired, and such an analysis can be used for diagnoses of a ventilation function, a function of the pulmonary blood stream of the lung field R. However, since the dose of radiation emitted in each photographing process as described above varies, it cannot be determined whether the shades of the inside of each frame image are caused by the amount of air, the amount of the blood stream, or the like received into the lung field R as described above or by variations in the dose of emitted radiation, and there is a possibility that an error occurs in the diagnosis performed by viewing the dynamic-state image.

Thus, in JP 2001-305232 A, a technology for controlling the dose of radiation emitted from a radiation generating device by detecting radiation that is emitted from a radiation generating device and is transmitted through a subject or a radiographic image photographing device and feeding back the dose of detected radiation to the radiation generating device is disclosed. In addition, in JP 2002-253541 A, a technology for storing the dose (a total amount thereof) of radiation that is necessary for photographing in a radiographic image photographing device in advance and determining the dose of the radiation emitted to a subject based on the dose (a total amount thereof) and the radiation transmitted through a predetermined area of the subject is disclosed.

According to both the technologies disclosed in JP 2001-305232 A and JP 2002-253541 A, the dose of radiation emitted from the radiation generating device is adjusted by feeding back radiation after being transmitted through a subject or the like. However, by configuring as such, there is a problem at least in a case where the dynamic-state photographing (see FIG. 8) is performed.

In other words, in a case where dynamic-state photographing is performed by emitting radiation onto a subject a plurality of number of times, even when the dose of radiation emitted to the subject is the same for each photographing process, as illustrated in FIG. 8, for example, the bright level of at least a portion of the lung field R is different between the case of the maximal inspiratory level (see $T=t_0$ or $t_6$) and the case of the maximal expiratory level (see $T=t_3$). In other words, the transmitted amount of radiation for the portion of the lung field R, for example, is different between the case of the maximal inspiratory level and the case of the maximal expiratory level.

Nevertheless, in a case where the dose of radiation emitted from the radiation generating device is adjusted by feeding back radiation after being transmitted through the subject (in this case, the lung field R) as described above, for example, there is not much change in the brightness level of the lung field R between the case of the maximal inspiratory level (see $T=t_0$ or $t_6$) and the case of the maximal expiratory level (see $T=t_3$). For this reason, even by analyzing each frame image, the amount of air, the amount of the blood stream, or the like received into the lung field R, cannot be precisely acquired, and accordingly, a dynamic-state image (in other words, each frame image) cannot be used for diagnoses of the ventilation function, the function of the pulmonary blood stream, and the like of the lung field R.

In this way, for example, in the case of the dynamic-state photographing, in a case where the dose of radiation emitted from the radiation generating device is adjusted by feeding back the radiation after being transmitted through a subject, an image provided for a diagnosis or the like cannot be photographed. For this reason, in photographing acquiring a plurality of radiographic images by emitting radiation onto a subject a plurality of number of times including not only the dynamic-state photographing but, similarly, any other kind of photographing such as tomosynthesis photographing, it is natural to perform adjustment such that the dose of radiation emitted to a subject (in other words, the dose of radiation before being emitted to a subject) and the like are as the same as possible in each photographing process.

SUMMARY OF THE INVENTION

The present invention has been made in consideration of the points described above, and an object thereof is to provide a radiographic image photographing system capable of adjusting the dose of radiation emitted to a subject to be as the same as possible in each photographing process in photographing acquiring a plurality of radiographic images by emitting radiation onto a subject a plurality of number of times.

To achieve the abovementioned object, according to an aspect, a radiographic image photographing system that photographs a plurality of radiographic images by emitting radiation to a radiographic image photographing device through a subject a plurality of number of times, reflecting one aspect of the present invention comprises:

a radiation generating device configured to emit radiation;

the radiographic image photographing device including a plurality of radiation detecting elements arranged in a two-dimensional pattern and configured to read a signal value from each of the radiation detecting elements;

a dose detecting unit arranged between the radiation generating device and the subject and configured to be able to detect a dose of radiation emitted to the subject; and a control unit configured to control the radiation generating device such that the dose of the radiation emitted to the subject becomes a target dose, wherein the control unit is configured to set a tube current or a mAs value of the radiation generating device such that the dose of the radiation emitted to the subject becomes the target dose, and corrects and sets the tube current or the mAs value in a case where a difference occurs between the dose of the radiation detected by the dose detecting unit and the target dose.

To achieve the abovementioned object, according to an aspect, a radiographic image photographing system that photographs a plurality of radiographic images by emitting radiation to a radiographic image photographing device through a subject a plurality of number of times, reflecting one aspect of the present invention comprises:

a radiation generating device configured to emit radiation;

the radiographic image photographing device including a plurality of radiation detecting elements arranged in a two-dimensional pattern and configured to read a signal value from each of the radiation detecting elements; and a control unit configured to control the radiation generating device such that the dose of the radiation emitted to the subject becomes a target dose when the radiation is emitted a plurality of number of times, wherein the control unit controls the radiation generating device such that information of a voltage and/or a current in the radiation generating device at the time of emitting radiation from the radiation generating device is the same as information of a voltage and/or a current in the radiation generating device at the time of emitting radiation of the target dose from the radiation generating device in the past.

To achieve the abovementioned object, according to an aspect, a radiographic image photographing system that photographs a plurality of radiographic images by emitting radiation to a radiographic image photographing device through a subject a plurality of number of times, reflecting one aspect of the present invention comprises:

a radiation generating device configured to emit radiation;

the radiographic image photographing device including a plurality of radiation detecting elements arranged in a two-dimensional pattern and configured to read a signal value from each of the radiation detecting elements;

a dose detecting unit arranged between the radiation generating device and the subject and configured to be able to detect a dose of radiation emitted to the subject; and an image processing device configured to generate a radiographic image based on the signal value read by the radiographic image photographing device every time radiation is emitted, wherein the image processing device corrects the signal value based on the dose of the radiation detected by the dose detecting unit immediately before the signal value is read by the radiographic image photographing device and generates the radiographic images such that each of the radiographic images is in a state being photographed while radiation of the same dose is emitted to the subject.

To achieve the abovementioned object, according to an aspect, a radiographic image photographing system that photographs a plurality of radiographic images by emitting radiation to a radiographic image photographing device through a subject a plurality of number of times, reflecting one aspect of the present invention comprises:

a radiation generating device configured to emit radiation;

the radiographic image photographing device including a plurality of radiation detecting elements arranged in a two-dimensional pattern and configured to read a signal value from each of the radiation detecting elements; and an image processing device configured to generate a radiographic image based on the signal value read by the radiographic image photographing device every time radiation is emitted, wherein the image processing device corrects the signal value based on information of a voltage and/or a current in the radiation generating device at the time of emitting radiation from the radiation generating device immediately before the signal value is read by the radiographic image photographing device and generates the radiographic images such that each of the radiographic images is in a state being photographed while radiation of the same dose is emitted to the subject.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of a radiographic image photographing system according to the present invention will be described with reference to the drawings. However, the scope of the invention is not limited to the illustrated examples.

Figure 1:
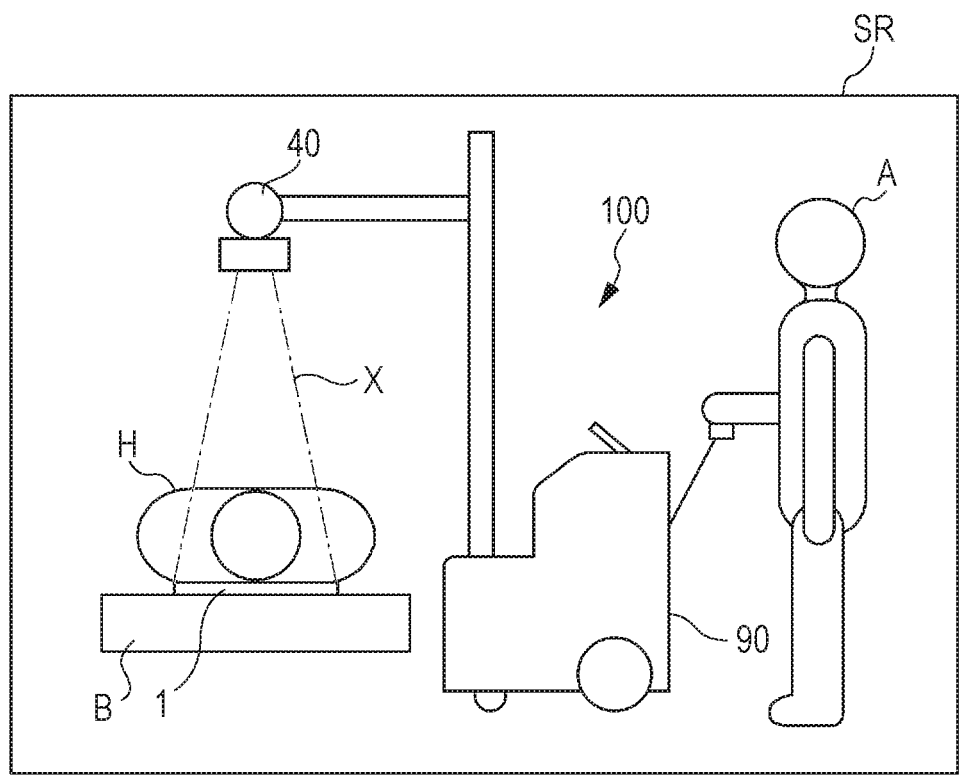
FIG. 1 is a diagram that illustrates a state in which a visiting car, in which a radiation generating device is mounted, is conveyed to a sickroom or the like, and photographing is performed by emitting radiation from the radiation generating device a plurality of number of times.

While the present invention is applied to a case where photographing is performed in a photographing room, for example, of a hospital or the like, for example, as illustrated in FIG. 1, the present invention may be applied also to a case where a visiting car 90, in which a radiation generating device 40 is mounted, is conveyed to a sickroom SR or the like, an operator A such as a radiology technician sets a radiographic image photographing device 1, for example, by inserting the device 1 between a patient who is a subject H and a bed B, and photographing is performed by emitting radiation X from the radiation generating device 40 a plurality of number of times.

Figure 3:
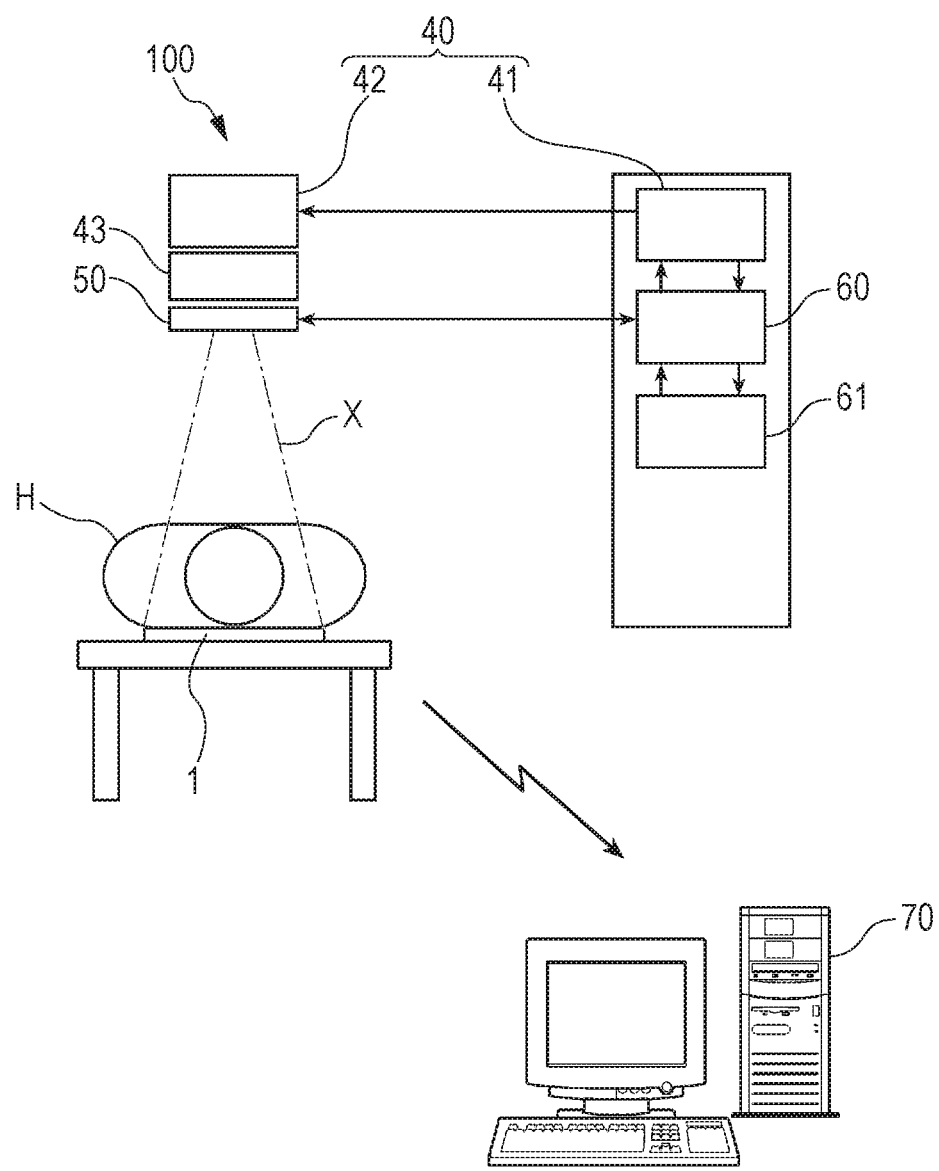
FIG. 3 is a diagram that illustrates a radiographic image photographing system according to a first embodiment.

In FIG. 1 and FIG. 3 and the like to be described later, while a case is illustrated in which photographing is performed in a state (in other words, a lying state) in which a patient who is a subject H lies down, the present invention is not limited thereto, but, for example, the invention is applied also to a case where photographing is performed in a state in which a patient stands up (in other words, a standing state).

Hereinafter, in order to simplify description, dynamic-state photographing and moving image photographing for photographing a plurality of radiographic images by emitting radiation X onto a subject H from a radiation generating device 40 a plurality of number of times, tomosynthesis photographing, photographing using a dual energy subtraction method, long-object photographing, and the like will be referred to as a series of photographing.

[Radiographic Image Photographing Device]

Here, a radiographic image photographing device used in a radiographic image photographing system according to each embodiment described below will be briefly described. Hereinafter, while a case will be described in which the radiographic image photographing device 1 is configured as a portable type, the radiographic image photographing device may be configured as a dedicated device type, for example, formed integrally with a supporting stand or the like.

Figure 2:
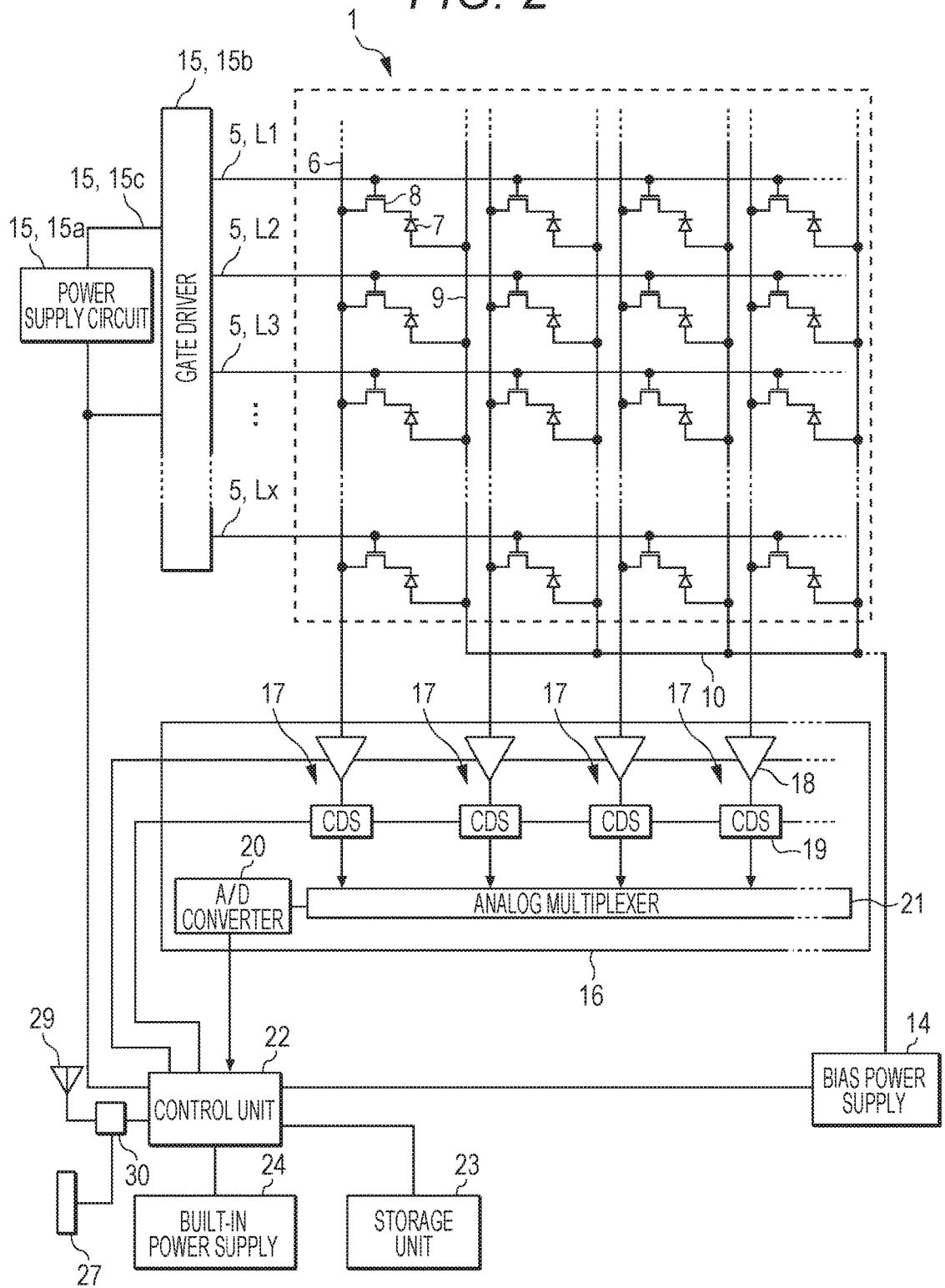
FIG. 2 is a block diagram that illustrates an equivalent circuit of a radiographic image photographing device.

FIG. 2 is a block diagram that illustrates an equivalent circuit of a radiographic image photographing device. As illustrated in FIG. 2, in the radiographic image photographing device 1, a plurality of radiation detecting elements 7 are arranged in a two-dimensional pattern (matrix pattern) on a sensor substrate not illustrated in the drawing. When radiation transmitted through a subject not illustrated in the drawing is emitted, each radiation detecting element 7 generates electric charge corresponding to the dose thereof. In addition, a reverse bias voltage is applied to each radiation detecting element 7 from a bias power supply 14 through a bias line 9 or a connection wire 10.

In a scan drive unit 15, switching between On voltage and Off voltage supplied from a power supply circuit 15a through a wiring 15c is performed by a gate driver 15b, and resultant voltages are applied to lines L1 to Lx of scan lines 5. A thin film transistor (TFT) 8 is connected to each radiation detecting element 7 as a switch element, and, when the Off voltage is applied through a scan line 5, the TFT 8 is in an Off state, blocks conduction between the radiation detecting element 7 and a signal line 6, and accumulates electric charge, which has been generated inside the radiation detecting element 7, inside the radiation detecting element 7. On the other hand, when the On voltage is applied through the scan line 5, the TFT 8 is in an On state and discharges electric charge, which has been accumulated inside the radiation detecting element 7, to the signal line 6.

Inside a read IC 16, a plurality of read circuits 17 are disposed, and each signal line 6 is connected to a corresponding read circuit 17. At the time of the process of reading a signal value from each radiation detecting element 7, when each TFT 8 connected to a scan line 5 to which the On voltage is applied from the gate driver 15b is in the On state, electric charge is discharged from the radiation detecting element 7 through the TFT 8 to the signal line 6 and flows into the read circuit 17. An amplification circuit 18 of the read circuit 17 outputs a voltage value corresponding to the amount of the electric charge flowing therein.

Then, a correlated double sampling circuit. (described as a "CDS" in FIG. 2) 19 reads the voltage value output from the amplification circuit 18 as an analog signal value D and outputs the read signal value to the downstream side. The output signal values D are sequentially transmitted to an A/D converter 20 through an analog multiplexer 21, are sequentially converted into digital signal values D by the A/D converter 20, and are sequentially stored in a storage unit 23. Then, by sequentially applying the On voltage lines L1 to Lx of the scan lines 5 from the gate driver 15b, the signal values D are read from the radiation detecting elements 7.

A control unit 22 is configured by a computer in which a central processing unit (CPU), a read only memory (ROM), a random access memory (RAM), an input/output interface, and the like are connected to a bus, a field programmable gate array (FPGA), and the like not illustrated in the drawing. The control unit 22 may be configured by a dedicated control circuit.

The storage unit 23 configured by a static RAM (SRAM), a synchronous DRAM (SDRAM), a NAND flash memory, or the like is connected to the control unit 22, and a communication unit 30 communicating with the outside through an antenna 29 or a connector 27 using a wireless system or a wired system, is connected to the control unit 22. In addition, the scan drive unit 15, the read circuit 17, the storage unit 23, and the bias power supply 14 described above and the like are connected to the control unit 22. In FIG. 2, while a case is illustrated in which the radiographic image photographing device 1 includes a built-in power supply 24, the radiographic image photographing device 1 may be configured to receive the supply of power from the outside.

The control unit 22 performs the process of reading the signal value D every time the radiation X is emitted by controlling the scan drive unit 15, each read circuit 17, and the like and stores the read signal values D in the storage unit 23 temporarily. Then, the control unit 22 transfers the signal value D stored in the storage unit 23 to an image processing device 70 (see FIGS. 3 and 6 and the like to be described later) every time the process of reading the signal value D is performed (in other words, every time radiation is emitted to the radiographic image photographing device 1). Alternatively, the control unit 22 may be configured to transfer each signal value D and the like to the image processing device 70 altogether after a series of photographing performed by emitting radiation a plurality of number of times ends.

In addition, in FIG. 3 and the like, while a case is illustrated in which each signal value D is transferred from the radiographic image photographing device 1 to the image processing device 70 by using a wireless system, each signal value D may be configured to be transferred to the image processing device 70 through a cable or the like not Illustrated in the drawing by using a wired system.

[Radiographic Image Generating Process Etc. in Image Processing Device]

The image processing device 70 performs image processing such as a so-called defective pixel correction, a normalization process, a dark correction, a gain correction, and gradation processing corresponding to a photographing portion (for example, the lung field R or the like) for each signal value D transferred from the radiographic image photographing device 1, thereby generating a radiographic image.

First Embodiment

Next, a radiographic image photographing system according to a first embodiment of the present invention will be described. FIG. 3 is a diagram that illustrates a radiographic image photographing system according to the first embodiment. In this embodiment, similar to each embodiment described below, a radiographic image photographing system 100 is a system (in other words, a system performing a series of photographing) that photographs a plurality of radiographic images (frame images) by emitting radiation X to a radiographic image photographing device 1 through a subject H a plurality of number of times.

The radiographic image photographing system 100 mainly includes the radiographic image photographing device 1 described above, a radiation generating device 40, a dose detecting unit 50, and a control unit 60 and further includes an image processing device 70.

The radiation generating device 40 includes a generator 41 and a radiation source 42. In the generator 41 of the radiation generating device 40, photographing conditions such as a tube voltage or a tube current (or a mAs value), the number of pulses of emitted radiation (in other words, the number of times of emitting radiation X in a series of photographing), and a pulse width (a time from the start of emission of radiation X to the end of the emission in one time of emission) can be set.

In a case where such photographing conditions are set, the generator 41 of the radiation generating device 40 controls the radiation source 42 so as to emit radiation X from the radiation source 42 with the set pulse width the set number of times by supplying the tube voltage, the tube current, and the like that are set to the radiation source 42.

While the radiation source 42 of the radiation generating device 40, for example, is configured to include a Coolidge X ray source, a rotating anode X ray source, or the like not illustrated in the drawing that is used in medical sites generally and widely, the radiation source 42 may be configured to include any other tubular bulb. The radiation source 42 is configured to emit radiation of a dose corresponding to the tube current or the mAs value set in the generator 41 as described above. In addition, in this embodiment, a collimator unit 43 in which a collimator (diaphragm) not illustrated in the drawing that is used for condensing the emission field of radiation X emitted from the radiation source 42 is built is arranged on a side of the radiation source 42 on which the radiation X is output.

The dose detecting unit 50 capable of detecting the dose of the radiation X emitted from the radiation source 42 is attached to a side of the collimator built in the collimator unit 43 from which the radiation X is output. In addition, the dose detecting unit 50, as illustrated in FIG. 3, may be attached to a side of the collimator unit 43 from which the radiation X is output or, while not illustrated in the drawing, be arranged inside the collimator unit 43 and, thus, may be attached to the side of the collimator from which the radiation X is output.

In addition, as the arrangement position of the dose detecting unit 50, while the dose detecting unit 50 may be configured to be attached to the collimator as in this embodiment, for example, the dose detecting unit 50 may be configured to be arranged at a position (in addition, a position not interrupting the photographing of a photographing portion) of a subject H disposed on the radiation source 42 side (in other words, the upper side of a subject H in FIG. 3) to which radiation X is emitted.

In this embodiment, by attaching the dose detecting unit 50 to the radiation X output side of the collimator in this way, the dose detecting unit 50 is arranged between the radiation source 42 of the radiation generating device 40 and the subject H.

In this embodiment, as the dose detecting unit 50, an area dosimeter is used, and the dose detecting unit 50 is configured to detect a dose area product (DAP) of radiation X that is emitted from the radiation source 42, has an emission field condensed by the collimator built in the collimator unit 43, and passes through the dose detecting unit 50.

As the dose detecting unit 50, other than that, a dosimeter such as a semiconductor detector may be used. In addition, the dose of the radiation X detected by the dose detecting unit 50 may be not an area dose, for example, but a dose per unit area or the like. For this reason, hereinafter, the area dose, the dose per unit area, and the like will be collectively referred simply to as a dose d of the radiation X.

Every time radiation X is emitted from the radiation source 42 of the radiation generating device 40, the dose detecting unit 50 is configured to detect a dose d of the radiation X and transmit the detected dose to the control unit 60.

In this embodiment, the control unit 60 is configured by a microcomputer disposed in the radiation generating device 40. However, other than that, for example, the generator 41 of the radiation generating device 40 may be configured to be used as the control unit 60. In addition, the control unit 60 may be configured as a device that is separate from the radiation generating device 40. A storage unit 61 configured by a hard disk drive (HDD), a non-volatile memory, or the like is connected to the control unit 60.

[Control of Radiation Generating Device Using Control Unit]

In this embodiment, while a series of photographing such as dynamic-state photographing is performed by emitting radiation X from the radiation generating device 40 a plurality of number of times as described above, the control unit 60 is configured to perform control of the radiation generating device 40 such that the dose d of the radiation X emitted to a subject H is a target dose dtarget every time the radiation X is emitted. At that time, the control unit 60 is configured to perform the control by setting a tube current or a mAs value described above (hereinafter, referred to as a tube current or the like) for the generator 41 of the radiation generating device 40. Hereinafter, a method used for the control will be specifically described.

Generally, calibration is performed regularly or as is necessary for the radiation generating device 40. Then, after the calibration, for a while, when a predetermined tube current I or the like is set in the generator 41 of the radiation generating device 40 at the time of performing a series of photographing, radiation X of a calibrated dose d corresponding to the tube current I or the like is emitted from the radiation source 42.

For this reason, in this embodiment, the tube current I or the like is set in the generator 41 of the radiation generating device 40 at the time of calibrating the radiation generating device 40 as the target dose dtarget described above, and the dose amount d (in other words, a calibrated dose dcalib) of the radiation X emitted from the radiation source 42 of the radiation generating device 40 is used.

However, when a time elapses after the calibration, even in a case where the same tube current I or the like is set in the generator 41 of the radiation generating device 40, the dose d of radiation X emitted from the radiation source 42 gradually decreases as the elapsed time becomes long (in other words, so-called settling occurs).

For this reason, in this embodiment, in order for the dose d of radiation X emitted to a subject H to be the target dose dtarget, the control unit 60 monitors the dose d of the actual radiation X that is detected and transmitted by the dose detecting unit 50 and, in a case where a difference between the dose d of the actual radiation X detected by the dose detecting unit 50 and the target dose dtarget occurs, corrects and sets the tube current I or the like in the generator 41 of the radiation generating device 40.

At that time, in this embodiment, the control unit 60 is configured to correct and set the tube current I or the like by instructing the generator 41 of the radiation generating device 40, for example, in the form of "increase the tube current I or the like by c %" or the like, and, hereinafter, "c" (percentage) of this case will be referred to as a correction value c. In other words, in a case where there is the above-described instruction from the control unit 60, the generator 41 of the radiation generating device 40 corrects and sets the tube current I or the like, which has been set by an operator A such as a radiology technician before the photographing, to be (1+c/100) times.

In addition, in a case where the control unit 60 is configured to instruct the generator 41 of the radiation generating device 40, for example, in the form of "multiply the tube current I or the like by c times thereof", the correction value c is a decimal, and, in a case where there is the above-described instruction from the control unit 60, the generator 41 of the radiation generating device 40 corrects and sets the set tube current I or the like to be c times thereof. In this way, the correction value c does not need to be necessarily represented as a percentage.

In this case, for example, it may be configured such that the control unit 60 has a relation equation, a graph, or the like representing a relation (in other words, a relation representing a value of the correction value c that is preferably set so as to adjust the dose d of the radiation X to the target dose dtarget) between the correction value c and the dose d of the radiation X in advance and, in a case where a dose d of the radiation X is transmitted from the dose detecting unit 50, calculates a correction value c based on the dose and the relation described above.

Figure 8:
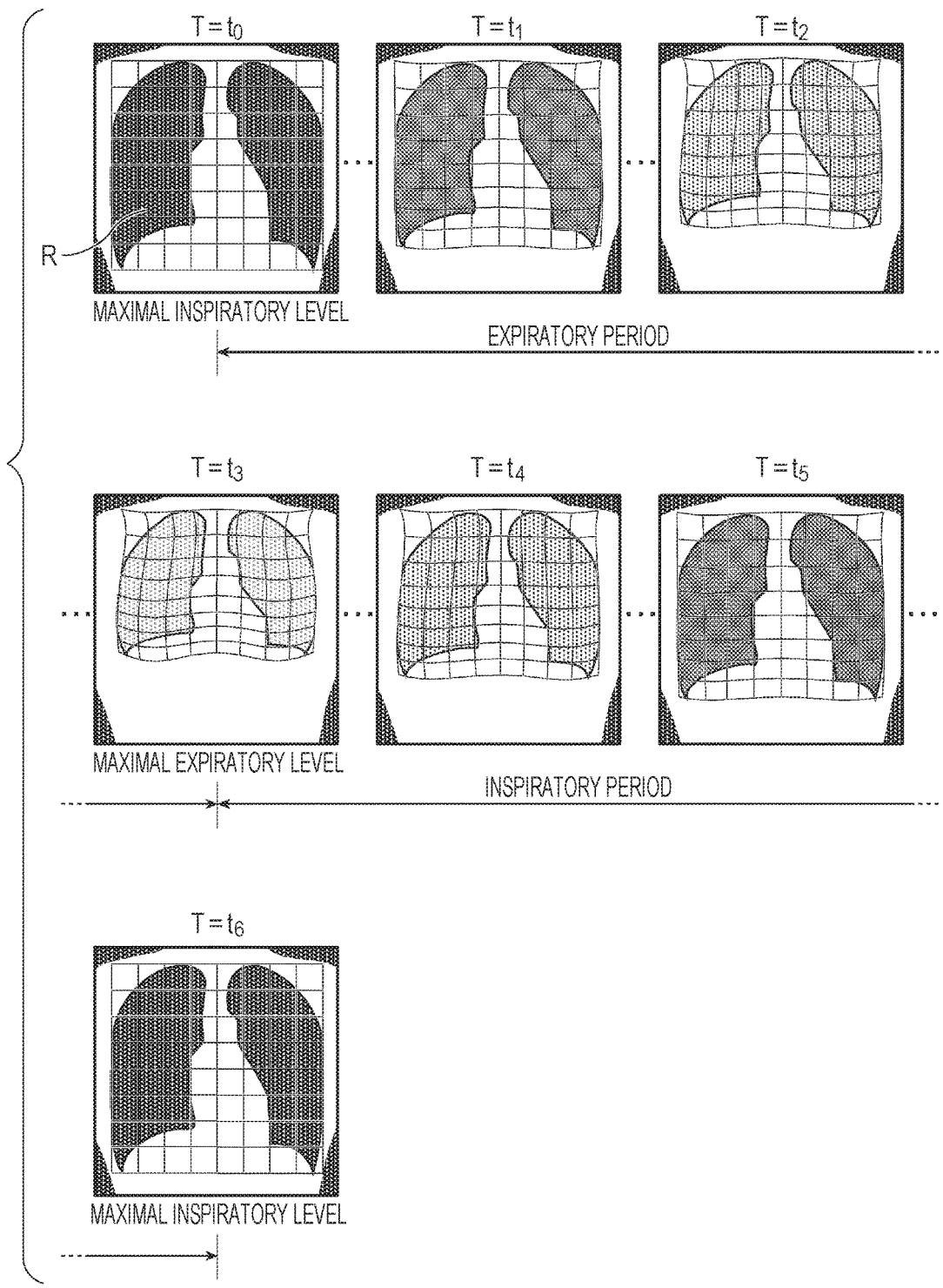
FIG. 8 is a diagram that illustrates each frame image photographed in dynamic-state photographing of a lung field of a patient who is a subject.

Meanwhile, in first photographing (for example, photographing for photographing a frame image of $T=t_0$ in dynamic-state photographing illustrated in FIG. 8) in a series of photographing as described above, in a case where the correction value c described above is to be calculated, the emission of radiation X has not been started, and data of the dose d of the radiation X has not been transmitted from the dose detecting unit 50. For this reason, the control unit 60 cannot calculate the correction value c of the tube current I or the like.

Thus, at the time of first photographing in a series of photographing, the control unit 60 may be configured not to perform a process of correcting and setting the tube current I or the like for the generator 41 of the radiation generating device 40. In such a case, the image processing device 70 may be configured not to generate a radiographic image based on a signal value D acquired by the first photographing or to discard a generated radiographic image. At the time of performing the first photographing, the detection of the dose d of the radiation X is performed by the dose detecting unit 50.

However, in this embodiment, for a correction value c at the time of performing the first photographing in a series of photographing, the control unit 60 is configured to correct the tube current I or the like by using a correction value cold, which is a correction value at the time of correcting the tube current I or the like in the past photographing, as the correction value c and set the corrected tube current I or the like in the generator 41 of the radiation generating device 40. For this reason, in this embodiment, for example, every time a correction value c is calculated for giving an instruction to the generator 41 of the radiation generating device 40, the control unit 60 stores the calculated correction value c in the storage unit 61 (see FIG. 3) as a correction value cold.

Then, in order to calculate a correction value c that is a correction value at the first photographing in a series of photographing, the control unit 60, for example, is configured to extract a latest correction value cold (in other words, a correction value cold that has been calculated last among past correction values c and stored in the storage unit 61) among correction values cold, which have been calculated in the past, stored in the storage unit 61 and use the extracted correction value as the correction value c at the time of the first photographing in the series of photographing performed from now on.

In addition, as described above, after the calibration of the radiation generating device 40 is performed, in a case where a predetermined tube current I or the like is set in the generator 41 of the radiation generating device 40 at the time of performing a series of photographing for the first time, radiation X of a dose d (in other words, the calibrated dose dcalib described above and the target dose dtarget in this embodiment) corresponding to the tube current I or the like is emitted from the radiation source 42, and accordingly, at the time of performing the first photographing in a series of photographing, the tube current I or the like does not need to be corrected. For this reason, there is no need to use the correction value cold that is a correction value at the time of correcting the tube current I or the like at the time of performing photographing in the past.

In this way, in a case where the calibration of the radiation generating device 40 is perform, thereafter, in performing a series of photographing for the first time, the correction value cold at the time of correcting the tube current I or the like at the time of performing photographing in the past is not necessary. Accordingly, in this embodiment, when the calibration of the radiation generating device 40 is performed, the past correction value cold is erased from the storage unit 61.

In addition, since the past correction value cold also represents degradation of the radiation source 42 of the radiation generating device 40 over time, the past correction value cold may be configured to remain in the storage unit 61 and be used for a determination of the degradation over time or the like, or the past correction value cold may be configured to be output to an external device at the time of performing calibration or the like.

[Operation]

Next, the operation of the radiographic image photographing system 100 according to this embodiment will be described.

First, a case will be described in which, after the calibration of the radiation generating device 40 is performed, a series of photographing such as moving image photographing is performed for the first time.

As described above, an operator A such as a radiology technician, before a series of photographing, sets photographing conditions such as a tube voltage or a tube current (or a mAs value, in other words, the tube current I or the like described above), the number of pulses of radiation, and a pulse width by inputting the photographing conditions to the generator 41 of the radiation generating device 40. In addition, such photographing conditions and the like may be configured to be automatically input to the generator 41 based on photographing order information or the like.

Then, the control unit 60 starts up the dose detecting unit 50. The dose detecting unit 50 may be configured to be manually started up by the operator A or the like.

In such a case, in a series of photographing performed first after the calibration of the radiation generating device 40 and in the first photographing among the series of photographing as described above, from the radiation source 42 of the radiation generating device 40, radiation X of a dose d corresponding to a predetermined tube current I or the like set in the generator 41, in other words, a calibrated dose dcalib is emitted.

Figure 4:
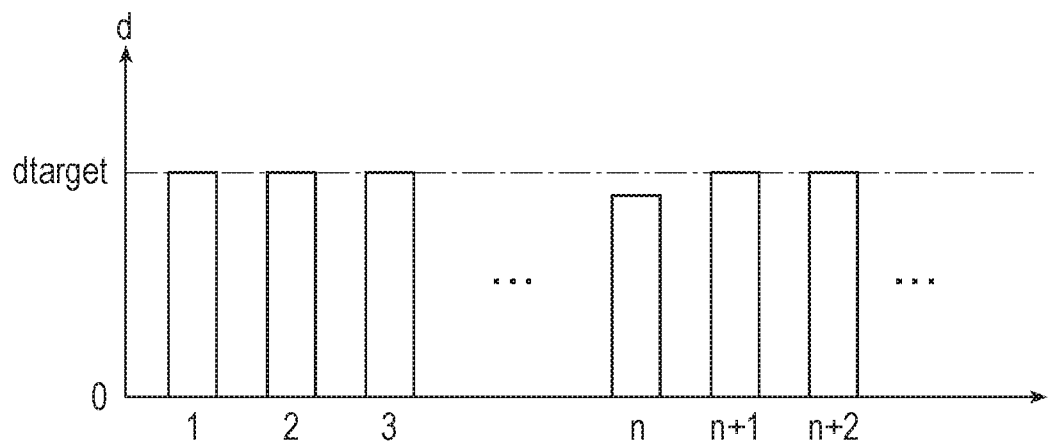
FIG. 4 is a diagram illustrating that a dose is returned to a target dose by performing control based on a correction value in a case where the dose of radiation detected by a dose detecting unit deviates from the target dose.

For this reason, as illustrated in FIG. 4, the dose d of the radiation X detected by the dose detecting unit 50 is the target dose dtarget (see "1" in FIG. 4). In this case, since the dose d of the emitted radiation X is the target dose dtarget, the control unit 60 does not correct the tube current I or the like.

The control unit 60 may be configured to necessarily refer to a correction value cold, which has been calculated in the past, stored in the storage unit 61 in the first photographing among the series of photographing regardless whether or not the calibration of the radiation generating device 40 is performed. Even configured as such, by configuring the past correction value cold to be erased from the storage unit 61 when the calibration of the radiation generating device 40 is performed as described above, a target to be referred to is not stored in the storage unit 61, and accordingly, the control unit 60 does not correct the tube current I or the like in the first photographing among the series of photographing performed first after the calibration of the radiation generating device 40.

In addition, in the series of photographing, also in second photographing and subsequent photographing, there are cases where the dose d of the emitted radiation X is the calibrated dose dcalib, and the dose d of the radiation X detected by the dose detecting unit 50 is the target dose dtarget, and the dose d of the radiation X emitted from the radiation source 42 is maintained. In such a case, the control unit 60 does not correct the tube current I or the like while the dose d of the radiation X detected by the dose detecting unit 50 is the target dose dtarget.

However, for example, when the radiation X is emitted from the radiation source 42 in the n-th photographing among the series of photographing, there are cases where the dose d of the radiation X detected by the dose detecting unit 50 deviates from the target dose dtarget (see "n" in FIG. 4) Then, at this time point, the control unit 60 calculates a correction value c based on the dose d of the radiation X detected by the dose detecting unit 50 and the relation described above.

Then, the control unit 60 corrects and sets the tube current I or the like, for example, by instructing the generator 41 of the radiation generating device 40 to "increase the tube current I or the like by c %". Then, when the correction value c is calculated as described above, the control unit 60 stores the calculated correction value c in the storage unit 61 as a correction value cold.

In this case, for example, the process of giving the above-described instruction to the generator 41 of the radiation generating device 40 from the control unit 60 may be configured to be repeated for each photographing process of (n+1)-th photographing and subsequent photographing. Furthermore, when the control unit 60 gives the above-described instruction, the generator 41 of the radiation generating device 40 may be configured to overwrite the tube current I or the like written in the memory so as to store the tube current I or the like that has been corrected (in other words, in this embodiment, a tube current I or the like that is multiplied by (1+c/100)) in the memory.

In this way, in the (n+1)-th photographing and the subsequent photographing among the series of photographing, since the generator 41 of the radiation generating device 40 sets the corrected tube current I or the like in the radiation source 42, as illustrated in FIG. 4, the dose d of the radiation X emitted (n+1)-th or later from the radiation source 42 of the radiation generating device 40 increases to be returned to the calibrated dose dcalib, and the dose d of the radiation X detected by the dose detecting unit 50 is returned to the target dose dtarget (see "n+1" and the like in FIG. 4).

For this reason, the dose d of the radiation X emitted to the subject H in each photographing among the series of photographing can be controlled to be the calibrated dose dcalib, in other words, the target dose dtarget.

On the other hand, in a next series of photographing (in other words, a next series of photographing performed when a time elapses after the calibration of the radiation generating device 40) after the series of photographing, even in a case where an operator A such as a radiology technician sets the tube current I or the like in the generator 41 of the radiation generating device 40 before the series of photographing, it cannot be determined that the dose d of radiation X emitted from the radiation source 42 of the radiation generating device 40 becomes a calibrated dose dcalib corresponding to a predetermined tube current I or the like set in the generator 41 (in other words, it cannot be determined that the dose d of the radiation X detected by the dose detecting unit 50 becomes the target dose dtarget).

Thus, in this embodiment, as described above, the control unit 60, for example, reads a latest correction value cold among correction values cold, which have been calculated in the past, stored in the storage unit 61 as the correction values c at the time of performing the first photographing among a series of photographing, sets the read correction value cold as the correction value c, and corrects and sets the tube current I or the like set by the operator A, for example, by instructing the generator 41 of the radiation generating device 40 to "increase the tube current I or the like by c %".

The state of the radiation source 42 of the radiation generating device 40 is considered not to be changed much from the state at the time of performing the series of photographing of the previous time. For this reason, for example, by using the latest correction value cold (the correction value cold that has been corrected last in the series of photographing of the previous time) as the correction value c of the first photographing among a series of photographing of this time as described above, the dose d of the radiation X emitted to the subject H in the first photographing among the series of photographing of this time can be adjusted to the calibrated dose dcalib, in other words, the target dose dtarget. At least, the dose d of the radiation X emitted to the subject H in the first photographing among the series of photographing of this time can be adjusted to a value not deviating much from the target dose dtarget.

Also in this case, as illustrated in FIG. 4, in a case where the dose d of the radiation X detected by the dose detecting unit 50 during the series of photographing deviates from the target dose dtarget (see "n" illustrated in FIG. 4), the control unit 60 calculates a correction value c based on the dose d of the radiation X detected by the dose detecting unit 50 and the relation described above and corrects and sets the tube current I or the like by giving an instruction to the generator 41 of the radiation generating device 40.

For this reason, also in this case, the dose d of the radiation X emitted to the subject H in the photographing of each time among the series of photographing can be controlled to be the calibrated dose dcalib, in other words, the target dose dtarget.

In addition, even in a case where the tube current I or the like is corrected as described above, as illustrated in FIG. 5, there are also cases where the dose d of the radiation X emitted in the first photographing among the series of photographing deviates from the target dose dtarget (see "1" illustrated in FIG. 5). However, in such cases, the control unit 60, similar to the case illustrated in FIG. 4, calculates a correction value c based on the dose d of the radiation X detected by the dose detecting unit 50 and the relation described above and corrects and sets the tube current I or the like in the generator 41 of the radiation generating device 40, and accordingly, in the second photographing and the subsequent photographing among the series of photographing, the dose d of the emitted radiation. X can be returned to the target dose dtarget (see "2" and the like illustrated in FIG. 5).

In this way, in this embodiment, an operator A such as a radiology technician, before a series of photographing, only sets the tube current I or the like by inputting it to the generator 41 of the radiation generating device 40 or inputs such photographing conditions and the like from photographing order information or the like, thereafter, the control unit 60 monitors the dose d of the radiation X transmitted from the dose detecting unit 50, represents the correction value c in the generator 41 of the radiation generating device 40 as is necessary, and automatically corrects and sets the tube current I or the like. For this reason, the dose d of the radiation X emitted to the subject H in photographing of each time among the series of photographing is automatically adjusted to the target dose dtarget.

[Effects]

As described above, according to the radiographic image photographing system 100 of this embodiment, in a series of photographing, in other words, in photographing acquiring a plurality of radiographic images by emitting radiation X to a subject H a plurality of number of times, for each photographing process among the series of photographing, the dose d of the radiation X emitted to the subject H can be automatically adjusted to be as the same as possible (in other words, to be the target dose dtarget).

For this reason, the occurrence of variations in the dose d of the emitted radiation X can be precisely suppressed, and, in radiographic images (in the case of a moving image photographing, frame images (for example, see FIG. 8)) generated by the image processing device 70, the occurrences of variations in the brightness levels of images in accordance with variations in the doses d of emitted radiation X can be precisely prevented.

In addition, in this embodiment, not the dose d of radiation X after being transmitted through a subject H but the dose d (in other words, the dose d of radiation X before being emitted to the subject H) of radiation X emitted to the subject H as described above is adjusted to be the same for each photographing process. For this reason, for example, in a case where dynamic-state photographing as illustrated in FIG. 8 is performed, instead of the dose d of the radiation X after being transmitted through the subject H (in this case, the lung field R), the radiation X of the same dose d is emitted to the subject H, frame images can be photographed.

Then, as described above, by adjusting the dose d of the radiation X emitted from the radiation source 42 of the radiation generating device 40 by feeding back the dose d of the radiation X after being transmitted through the subject H, for example, there is not a large change between the brightness level of the lung field R in the case of the maximal inspiratory level (see $T=t_0$ or $t_6$) and the brightness level of the lung field R in the case of the maximal expiratory level (see $T=t_3$) illustrated in for example FIG. 8, and there are problems including a problem of not precisely acquiring the amount of air received into the lung field R, the amount of the blood stream, and the like by even analyzing each frame image.

However, in the radiographic image photographing system 100 according to this embodiment, as described above, the dose d of the radiation X is adjusted based on the dose d (the dose d of the radiation X before being emitted to the subject H) of the radiation X emitted to the subject H, and accordingly, for example, photographing can be performed in a state in which the brightness level of the lung field R in the case of the maximal inspiratory level (see $T=t_0$ or $t_6$ illustrated in FIG. 8) and the brightness level of the lung field R in the case of the maximal expiratory level (see $T=t_3$) can be clearly distinguished. For this reason, the amount of air, the amount of the blood stream, and the like received in the lung field R can be precisely analyzed by analyzing each frame image, and accordingly, a dynamic-state image (in other words, frame images) can be used for a diagnosis of the ventilation function, the function of the pulmonary blood stream, and the like of the lung field R.

In addition, in this embodiment, the tube current I or the like is corrected and set by using the correction value cold at the time of correcting the tube current I or the like at the time of performing photographing in the past as the correction value c at the time of performing the first photographing among a series of photographing, and accordingly, the dose d of the radiation X emitted to the subject H in the first photographing among the series of photographing can be adjusted to the target dose dtarget, and the dose d of the radiation X emitted to the subject H at least in the first photographing can be set to a value not deviating much from the target dose dtarget. For this reason, also from this point, the occurrence of variations in the dose d of the emitted radiation X can be precisely suppressed.

In addition, depending on the radiation generating device 40, not only the dose d of the radiation X emitted from the radiation source 42 varies as described above (in other words, the dose d gently goes up and down over time), but there are also cases where the dose d varies each time when the radiation X is emitted (in other words, the dose d delicately goes up and down for each photographing process).

Then, also in such cases, the control unit 60 may be configured to perform completely the same control as that of the embodiment described above, and, every time the dose d of the radiation X emitted from the radiation source 42 deviates from the target dose dtarget, correct and set the tube current I or the like in the generator 41 of the radiation generating device 40.

In addition, in the case described above, it may be configured such that a variation of a certain degree in the dose d of the radiation X is allowed, the correction of the above-described tube current I or the like described in this embodiment is not performed (or the calculated correction value c is not changed) in a case where an error in the dose d of the radiation X detected by the dose detecting unit 50 from the target dose dtarget is within a predetermined range, and, the correction of the tube current I or the like according to this embodiment is performed (or a correction value c is newly calculated) in a case where the error in the dose d of the radiation X from the target dose dtarget exceeds the predetermined range.

Furthermore, in a case where the dose d of the radiation X emitted from the radiation source 42 finely varies for each photographing process as described above, even when the latest correction value cold in the series of photographing of the previous time is used as the correction value c at the time of performing the first photographing in a series of photographing, the dose d of the radiation X is not necessarily corrected precisely to the target dose dtarget. For this reason, in such a case, instead of using the latest correction value cold, for example, a moving average of correction values cold, which corresponds to a predetermined number of times, calculated in the past including the latest correction value c may be configured to be used.

In this way, a method of selecting a correction value cold at the time of correcting the tube current I or the like in the past photographing is determined appropriately in accordance with the characteristics (for example, variations in the dose d of the emitted radiation X) of the radiation source 42 of the radiation generating device 40 or the like.

Second Embodiment

Next, a radiographic image photographing system according to a second embodiment of the present invention will be described. Here, a same reference numeral as that of the first embodiment will be assigned to a unit, a device, or the like having the same function as that of the first embodiment.

Figure 6:
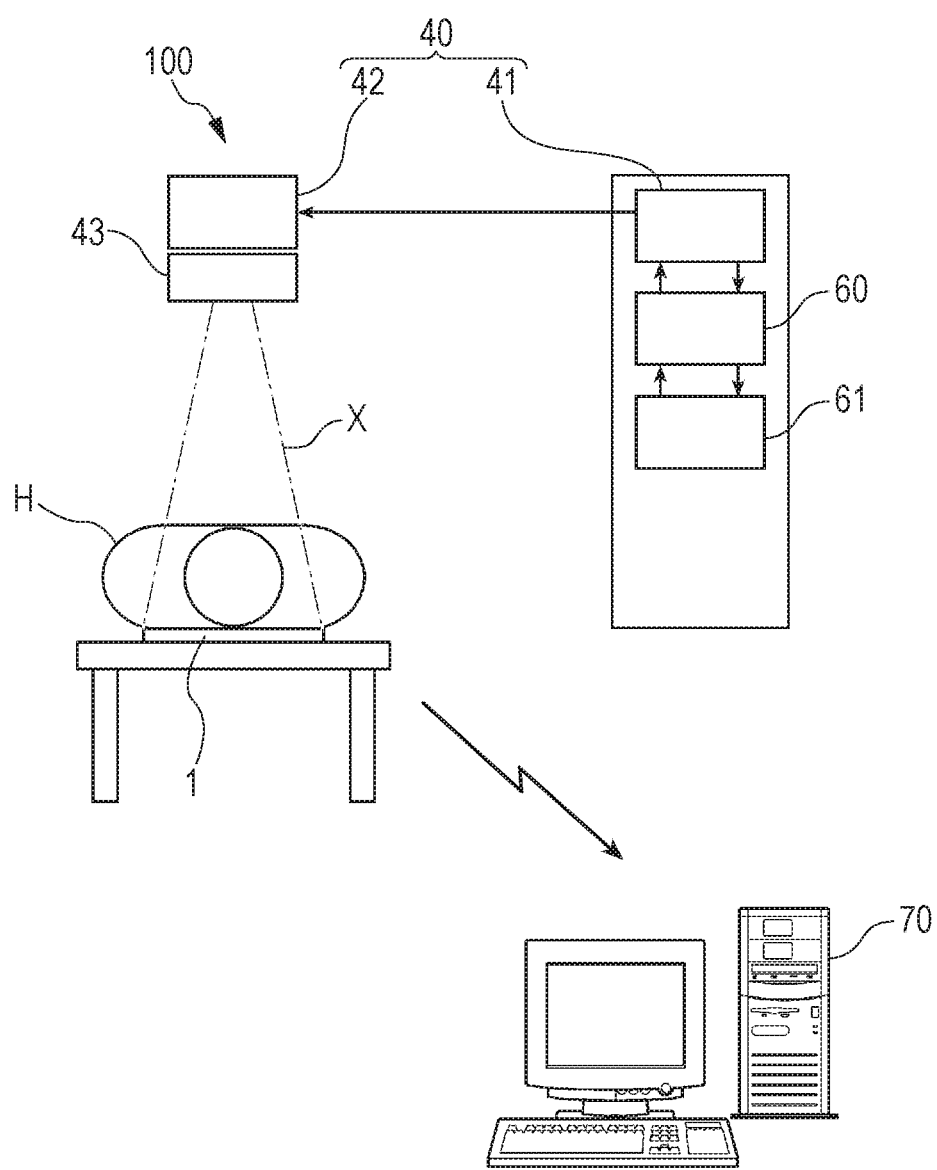
FIG. 6 is a diagram that illustrates a radiographic image photographing system according to a second embodiment.

FIG. 6 is a diagram that illustrates a radiographic image photographing system according to the second embodiment.

Similar to the first embodiment, also in this embodiment, the control unit 60 is configured to perform control of the radiation generating device 40 such that the dose d of radiation X emitted to a subject H is a target dose dtarget (in other words, for example, a calibrated dose dcalib) when the radiation X is emitted a plurality of number of times in a series of photographing.

In the first embodiment described above, it is determined whether or not "settling" occurs in the radiation generating device 40 (in other words, whether or not, even in a case where the tube current I or the like is set in the generator 41 of the radiation generating device 40, the dose d of radiation X that is actually emitted is not the calibrated dose dcalib but decreased to be less than the calibrated dose dcalib) by detecting the dose d of the radiation X emitted from the radiation source 42 of the radiation generating device 40 using the dose detecting unit 50.

However, when the tube current I or the like is set in the generator 41 of the radiation generating device 40, it can be determined whether the dose d of the radiation X emitted from the radiation source 42 is the calibrated dose dcalib based on an actual voltage v or current i in the generator 41 of the radiation generating device 40 without detecting the dose using the dose detecting unit 50 as described above.

In other words, even in a case where a predetermined tube current I or the like is set in the generator 41 of the radiation generating device 40, when "settling" occurs in the radiation generating device 40, compared to a case where the radiation X of the calibrated dose dcalib is emitted, a voltage v or current i in the generator 41 of the radiation generating device 40 changes.

Thus, in this embodiment, the control unit 60 is configured to perform control of a generator 41 of the radiation generating device 40 such that information of a voltage v or a current i in the generator 41 of the radiation generating device 40 at the time of emitting radiation X from the radiation source 42 of the radiation generating device 40 is the same as information of a voltage void or a current iold in the generator 41 at the time of emitting the radiation X of a target dose dtarget (in other words, regarded as a calibrated dose dcalib also in this embodiment) from the radiation source 42 of the radiation generating device 40 in the past.

By performing control of the generator 41 such that, the information of the voltage v and the current i in the generator 41 of the radiation generating device 40 is the same as the information of the voltage void or the current iold in the generator 41 at the time of emitting the radiation X of the target dose dtarget from the radiation source 42 of the radiation generating device 40 in the past, the dose d of the radiation X emitted from the radiation source 42 of the radiation generating device 40 at each photographing process in a series of photographing can be adjusted to the calibrated dose dcalib and can be adjusted to the target dose dtarget.

In addition, as described above, as the information of the voltage void or the current iold in the generator 41 at the time of emitting the radiation X of the target dose dtarget from the radiation source 42 of the radiation generating device 40 in the past, information of a voltage void or a current iold in the radiation generating device 40 at the time of performing calibration of the radiation generating device 40 performed in the past may be configured to be used.

By configuring as such, the control unit 60 can perform control of the generator 41 such that the information of the voltage v and the current i in the generator 41 of the radiation generating device 40 is the same as the information of the voltage void or the current iold in the radiation generating device 40 at the time of emitting the radiation X from the radiation source 42 at the time of performing calibration of the radiation generating device 40 performed in the past, and the dose d of the radiation X emitted from, the radiation source 42 of the radiation generating device 40 at the time of performing each photographing process in a series of photographing can be adjusted to the calibrated dose dcalib (in other words, the target dose dtarget).

Figure 7:
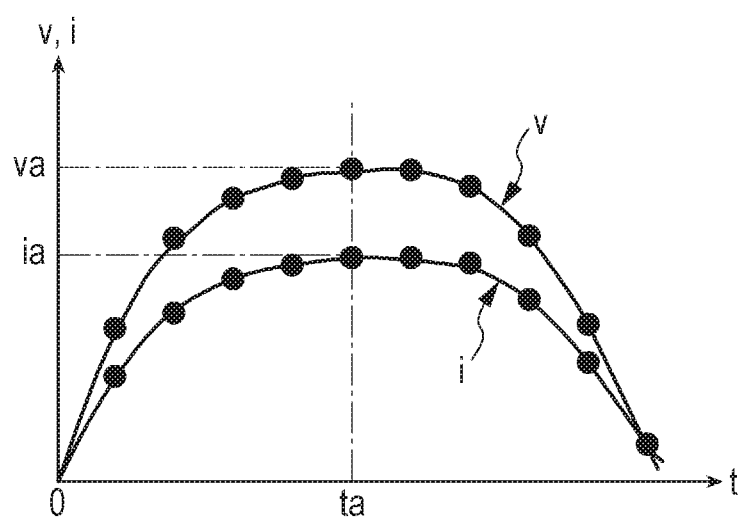
FIG. 7 is a diagram that illustrates waveforms of a case where a voltage and a current in a generator of the radiation generating device at the time of emitting radiation from a radiation source are sampled with respect to time.

By sampling the voltage v and the current i in the generator 41 at the time of emitting radiation X from the radiation source 42 of the radiation generating device 40 with respect to time, for example, waveforms of the voltage v and the current i as illustrated in FIG. 7 can be acquired. Thus, the waveforms of the voltage v and the current i in the generator 41 of the radiation generating device 40 acquired in this way can be configured to be used as the information of the voltage v and the current i in the generator 41 of the radiation generating device 40.

In this case, for example, the control unit 60 may be configured to sample the voltage v or the current i described above output from the generator 41 of the radiation generating device 40. Alternatively, it may be configured such that the sampling is performed by the generator 41 of the radiation generating device 40, and a result thereof (see FIG. 7) is output to the control unit 60.

In such a case, the control unit 60 may be configured to monitor the waveform (see FIG. 7) of the sampled voltage v or current i in the generator 41 and, for example, in a case where deformation from the waveform of the voltage void or the current bold in the radiation generating device 40 at the time of emitting the radiation X from the radiation source 42 at the time of performing calibration of the radiation generating device 40 performed in the past occurs (or in a case where the magnitude of the deformation exceeds a predetermined allowed range), determine that the dose d of the emitted radiation X deviates from the target dose dtarget.

In a case where the dose d of the emitted radiation X deviates from the target dose dtarget, the control unit 60, for example, may be configured to transmit the waveform of the voltage void or the current iold in the radiation generating device 40 at the time of emitting the radiation X from the radiation source 42 at the time of performing calibration of the radiation generating device 40 performed in the past to the generator 41 of the radiation generating device 40 and control the generator 41 of the radiation generating device 40 to apply a feedback such that waveforms of the voltage v and the current i in the generator 41 at the time of emitting the radiation X from the radiation source 42 of the radiation generating device 40 are the waveforms.

Alternatively, as described above, instead of transmitting the information of the voltage void or the current iold of the past to the generator 41 of the radiation generating device 40, the control unit 60 may be configured to transmit the information every time the radiation X is emitted from the radiation source 42 of the radiation generating device 40 in a series of photographing (in other words, for each photographing process in the series of photographing) in a case where the information (for example, a waveform, the same in description presented below) of the voltage v and the current i in the generator 41 at the time of emitting radiation X from the radiation source 42 of the radiation generating device 40 is changed from information of the voltage v and the current i of the past.

In addition, the control unit 60 may be configured to control the generator 41 of the radiation generating device 40 by transmitting the information of the voltage void or the current iold of the past before the start of a series of photographing to the generator 41 of the radiation generating device 40 (in other words, transmitting the information of the voltage void or the current iold of the past only once) and storing the information in the generator 41.

On the other hand, as the information of the voltage v and the current i in the generator 41 at the time of emitting radiation X from the radiation source 42 of the radiation generating device 40, for example, as illustrated in FIG. 7, a voltage va and a current ia at a time point when a time ta elapses after the start of the emission of the radiation X (t=0 illustrated in FIG. 7) may be configured to be used.

In addition, as the information of the voltage v and the current i in the generator 41 at the time of emitting radiation X from the radiation source 42 of the radiation generating device 40, for example, areas between a graph of the voltage v and a graph of the current i illustrated in FIG. 7 and the horizontal axis or the like may be configured to be calculated and used.

[Effects]

As above, also in the radiographic image photographing system 100 according to the second embodiment, similar to the case of the first embodiment described above, for each photographing process among a series of photographing, automatic adjustment can be performed such that the dose d of radiation X emitted to a subject H is as the same as possible (in other words, is the target dose dtarget).

For this reason, the occurrence of variations in the dose d of the emitted radiation X can be precisely suppressed, and, in radiographic images (in the case of a moving image photographing, frame images (for example, see FIG. 8) generated by the image processing device 70, the occurrences of variations in the brightness levels of images in accordance with variations in the doses d of emitted radiation X can be precisely prevented.

In addition, also in this embodiment, not the dose d of radiation X after being transmitted through a subject H but the dose d of radiation X emitted to the subject H (in other words, the dose d of radiation X before being emitted to the subject H) is adjusted to be the same for each photographing process. Accordingly, for example, in each frame image photographed through the dynamic-state photographing, advantageous effects similar to those of the case of the first embodiment can be acquired. In addition, in the second embodiment, there is also an advantage that the dose detecting unit 50 does not need to be included in the system.

Third Embodiment

In the first and second embodiments described above, the case has been described in which the dose d of radiation X emitted from the radiation source 42 of the radiation generating device 40 is adjusted in real time to the target dose dtarget based on the dose d of the radiation X detected by the dose detecting unit 50 (in the case of the first embodiment) or the information of the waveforms of the voltage v and the current i in the generator 41 at the time of emitting the radiation X from the radiation source 42 of the radiation generating device 40 (in the case of the second embodiment, hereinafter, simply referred to as the information of the voltage v and the current i in the generator 41).

However, depending on the configuration of the radiation generating device 40, the environment in which the series of photographing is performed, and the like, there are also cases where the dose d of the radiation X emitted from the radiation source 42 cannot be adjusted in real time by reflecting such information.

Thus, in such cases, when a radiographic image (a frame image in the case of moving-image photographing) is generated based on a signal value D read by the radiographic image photographing device 1 by the image processing device 70 (see FIGS. 3 and 6) as described above, it may be configured such that the signal value D read by the radiographic image photographing device 1 is corrected using the dose d of the radiation X detected by the dose detecting unit 50 or the information of the voltage v and the current n the generator 41, and a radiographic image is generated based on the corrected signal value D.

By configuring as such, unlike the first and second embodiments described above, while the dose d of the radiation X emitted from the radiation source 42 of the radiation generating device 40 cannot be adjusted to the target dose dtarget (for example, the calibrated dose dcalib), the influence of variations on the dose d of the emitted radiation X can be eliminated at least from the generated radiographic image, Hereinafter, description will be presented more specifically.

Figure 5:
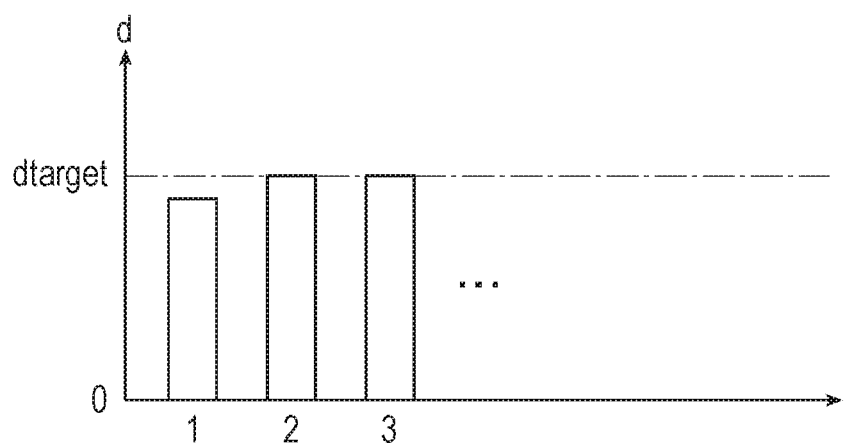
FIG. 5 is a diagram illustrating that, by performing control similar to that illustrated in FIG. 4, a dose is returned to a target dose also in a case where the dose of radiation deviates from the target dose in first photographing in a series of photographing.

In a third embodiment, in each photographing process in a series of photographing, similar to the case of the first embodiment illustrated in FIG. 3, the dose d of the radiation X is detected (see FIGS. 4 and 5) by the dose detecting unit 50 (see FIG. 3), or, similar to the case of the second embodiment illustrated in FIG. 5, the information of the voltage v and the current i in the generator 41 of the radiation generating device 40 is acquire d (see FIG. 7).

Then, such information (in other words, the dose d of the radiation X detected by the dose detecting unit 50 or the information of the voltage v and the current i in the generator 41 of the radiation generating device 40) may be configured to be directly transmitted from the dose detecting unit 50 or the generator 41 of the radiation generating device 40 to the image processing device 70, or the control unit 60 may be configured to acquire such information and transmit the information to the image processing device 70 as described above.

At that time, as described above, in a case where the signal value D is configured to be transferred from the radiographic image photographing device 1 to the image processing device 70 for each time when the process of reading the signal value D is performed (in other words, each photographing process in the series of photographing), by transmitting also the information together with the signal value D for each photographing process, while the series of photographing is performed, a radiographic image can be generated by correcting the signal value D based on the information in the image processing device 70.

Hereinafter, while the case will be described in which the information described above is transmitted in this way to the image processing device 70 together with the transmission of the signal value D for each photographing process in the series of photographing, as described above, after the end of the series of photographing, the signal value D may be configured to be transferred altogether from the radiographic image photographing device 1 to the image processing device 70. In such a case, the information described above may be configured to be transmitted to the image processing device 70 in each photographing process in the series of photographing or may be configured to be stored in the storage unit 61 temporarily and transmitted altogether after the end of the series of photographing.

Hereinafter, a case where the information described above is the dose d of the radiation X detected by the dose detecting unit 50 (see FIG. 3) will be described as an example. In addition, in a case where the information of the voltage v and the current i in the generator 41 of the radiation generating device 40 is transmitted as the information described above, the waveforms of the voltage v and the current i (see FIG. 7) may be configured to be transmitted, or a voltage va, a current ia, and the like at a time point when a time ta elapses after the start of the emission of the radiation X (t=0 illustrated in FIG. 7) may be configured to be transmitted as described above.

In such a case, the image processing device 70, for example, has a relation equation, a graph, or the tike representing a relation between a signal value D0 read by each radiation detecting element 7 of the radiographic image photographing device 1 in a case where the radiation X is emitted from the radiation source 42 of the radiation generating device 40 in a state in which the subject H is not present and the dose d of the radiation X emitted at that time in advance. Here, the signal value D0 read by each radiation detecting element 7 of the radiographic image photographing device 1 in a case where the radiation X of the target dose dtarget is emitted from the radiation source 42 of the radiation generating device 40 in the state in which the subject H is not present will be referred to as a signal value D0target.

Then, as described above, when the signal value D read by the radiographic image photographing device 1 and the dose d of the radiation X detected by the dose detecting unit 50 as the information described above (in other words, the dose d of the radiation X emitted immediately before the signal value is read by the radiographic image photographing device 1) are transmitted, the image processing device 70, first, calculates a signal value D0 read when the radiation X of the dose d is emitted based on the dose d of the radiation X detected by the dose detecting unit 50 and the relation described above.

Then, the image processing device 70 corrects the signal value D to a signal value D* of a case where the radiation X of the target dose dtarget is emitted by using the following Equation (1) for each radiation detecting element 7 of the radiographic image photographing device 1. Hereinafter, D* will be referred to as a signal value after correction.

$$D^* = D \times (D0\text{target}/D0) \qquad (1)$$

The image processing device 70, similar to the radiographic image generating process described above, is configured to generate a radiographic image by performing image processing such as a defective pixel correction, a normalization process, a dark correction, a gain correction, and gradation processing according to a photographing portion (for example, the lung field R or the like) for the signal value D* after correction.

By configuring as such, each generated radiographic image is in a state being photographed in a state in which the radiation X of the same dose d (in other words, the target dose dtarget) is emitted to the subject H, and, similar to the cases of the first and second embodiments described above, the occurrences of variations in the brightness levels of images in accordance with variations in the doses d of the emitted radiation X can be precisely prevented.

In addition, also in this embodiment, since the signal value D is configured to be corrected based on the relation between the signal value D0 read by each radiation detecting element 7 of the radiographic image photographing device 1 in a case where radiation X is emitted from the radiation source 42 of the radiation generating device 40 in the state in which the subject H is not presented as described above, instead of the dose d of radiation X after being transmitted through a subject H, and the dose d of the radiation X emitted at that time, the dose d of radiation X emitted to the subject H (in other words, the dose d of the radiation X before being emitted to the subject H) is in the state being adjusted to be the same for each photographing process (in other words, a state in which each radiographic image is photographed in a state in which radiation of the same dose is emitted to the subject. Accordingly, for example, in each frame image (see FIG. 8) photographed through the dynamic-state photographing, advantageous effects similar to those of the case of the first embodiment and the second embodiment can be acquired.

It is apparent that the present invention is not limited to each embodiment or the like described above, and each embodiment may be appropriately changed without departing from the concept of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiographic image photographing system that photographs a plurality of radiographic images by emitting radiation to a radiographic image photographing device through a subject a plurality of number of times, the radiographic image photographing system comprising:
    a radiation generating device configured to emit radiation, the radiographic image photographing device including a plurality of radiation detecting elements arranged in a two-dimensional pattern and configured to read a signal value from each of the radiation detecting elements;
    a dose detecting unit arranged between the radiation generating device and the subject and configured to detect a dose of radiation emitted to the subject; and
    an image processing device configured to generate a radiographic image based on the signal value read by the radiographic image photographing device every time radiation is emitted,
    wherein the image processing device (i) corrects the signal value based on the dose of the radiation which is detected by the dose detecting unit immediately before the signal value is read by the radiographic image photographing device, and (ii) generates the radiographic images such that each of the radiographic images is in a state being photographed while radiation of the same dose is emitted to the subject.

2. A radiographic image photographing system that photographs a plurality of radiographic images by emitting radiation to a radiographic image photographing device through a subject a plurality of number of times, the radiographic image photographing system comprising:
    a radiation generating device configured to emit radiation, the radiographic image photographing device including a plurality of radiation detecting elements arranged in a two-dimensional pattern and configured to read a signal value from each of the radiation detecting elements; and
    an image processing device configured to generate a radiographic image based on the signal value read by the radiographic image photographing device every time radiation is emitted,
    wherein the image processing device (i) corrects the signal value based on information of a voltage and/or a current in the radiation generating device at a time of emitting radiation from the radiation generating device which is immediately before the signal value is read by the radiographic image photographing device, and (ii) generates the radiographic images such that each of the radiographic images is in a state being photographed while radiation of the same dose is emitted to the subject.

* * * * *